United States Patent
Wada et al.

(10) Patent No.: US 10,398,653 B2
(45) Date of Patent: *Sep. 3, 2019

(54) SOLID PREPARATIONS CONTAINING TOFOGLIFLOZIN AND PROCESS OF PRODUCING THE SAME

(71) Applicant: CHUGAI SEIYAKU KABUSHIKI KAISHA, Tokyo (JP)

(72) Inventors: Kenta Wada, Tokyo (JP); Tomoaki Hirayama, Shizuoka (JP); Kenichi Sakai, Tokyo (JP); Shiho Yoshimura, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/260,530

(22) Filed: Jan. 29, 2019

(65) Prior Publication Data

US 2019/0151248 A1    May 23, 2019

Related U.S. Application Data

(63) Continuation of application No. 15/108,335, filed as application No. PCT/JP2014/084561 on Dec. 26, 2014, now Pat. No. 10,231,930.

(30) Foreign Application Priority Data

Dec. 27, 2013  (JP) .................................. 2013-273060

(51) Int. Cl.
*A61K 9/20* (2006.01)
*A61K 31/7048* (2006.01)

(52) U.S. Cl.
CPC .............. *A61K 9/2054* (2013.01); *A61K 9/20* (2013.01); *A61K 9/2018* (2013.01); *A61K 9/2059* (2013.01); *A61K 31/7048* (2013.01)

(58) Field of Classification Search
None
See application file for complete search history.

(56) References Cited

U.S. PATENT DOCUMENTS

| 5,747,068 A | 5/1998 | Mendizabal |
| 10,231,930 B2 * | 3/2019 | Wada .................. A61K 9/2018 |
| 2008/0234366 A1 * | 9/2008 | Bindra ................. A61K 9/1652 514/460 |
| 2009/0030006 A1 | 1/2009 | Kobayashi et al. |

(Continued)

FOREIGN PATENT DOCUMENTS

| JP | 08-040884 A | 2/1996 |
| JP | 2006-528689 A | 12/2006 |

(Continued)

OTHER PUBLICATIONS

Rinsho Shiken Joho. "JapicCTI-101349", http://www.clinicaltrials.jp/user/cteDetail.jsp?clinicalTrialid=8116, (Nov. 2012).

(Continued)

*Primary Examiner* — Robert A Wax
*Assistant Examiner* — Melissa S Mercier
(74) *Attorney, Agent, or Firm* — Browdy and Neimark, PLLC

(57) ABSTRACT

The present invention provides a method for producing a pharmaceutical composition which is a tablet and which contains tofogliflozin as an active ingredient. The method comprises mixing an additive and tofogliflozin to prepare a powder mixture and obtaining a tablet from the powder mixture by direct compression. The additive comprises at least one filler.

8 Claims, 2 Drawing Sheets

(56) References Cited

U.S. PATENT DOCUMENTS

2011/0014284 A1* 1/2011 Eisenreich ........... A61K 9/0019
424/465
2011/0306778 A1 12/2011 Murakata et al.
2013/0035281 A1 2/2013 Klein

FOREIGN PATENT DOCUMENTS

| JP | 2008-031183 A | 2/2008 |
| --- | --- | --- |
| WO | 2004/100880 A2 | 11/2004 |
| WO | 2006080421 A1 | 3/2006 |
| WO | 20090154276 A1 | 12/2009 |
| WO | 2012115249 A1 | 8/2012 |
| WO | 2012/163990 A1 | 12/2012 |
| WO | 2014/161836 A1 | 10/2014 |

OTHER PUBLICATIONS

Kitagawa, "Basic Yakugaku Kyokasho Series 20 Yakuzaigaku", Kagaku-Dojin Publishing Co., Inc., pp. 87-88 (Apr. 2013).
Apleway 20mg Tablets, Kanja Muke Iyakuhin Guide (May 2014).
International Search Report for corresponding International Patent Application No. PCT/JP2014/084561.
Matsumoto, Mitsuo, Ed., Manual of Pharmaceutics; Nanzando, Co., Ltd; Mar. 20, 1989; pp. 89, 107, and 108.
Extended European Search Report dated Aug. 21, 2017, in corresponding European Patent Application No. EP14874030.
Decision of Refusal dated Nov. 26, 2018 in corresponding Japanese Patent Appln. No. 2015-555053 with English Machine Translation.

* cited by examiner

SOLID PREPARATIONS CONTAINING TOFOGLIFLOZIN AND PROCESS OF PRODUCING THE SAME

TECHNICAL FIELD

The present invention relates to solid preparations containing tofogliflozin, namely, 1,1-Anhydro-1-C-[5-(4-ethylphenyl)methyl-2-(hydroxymethyl)phenyl]-β-D-glucopyranose, which is a spiroketal derivative, and the process of producing the preparations.

BACKGROUND ART

A spiroketal derivative having a certain structure has been known as being useful for preventing or treating diabetes (Patent Documents 1 and 2). For example, WO 2006/080421 (Patent Document 1) discloses a compound represented by the following formula (I), generic name of which is tofogliflozin (chemical name: 1,1-Anhydro-1-C-[5-(4-ethylphenyl)methyl-2-(hydroxymethyl)phenyl]-β-D-glucopyranose), and states that the compound has an excellent inhibitory activity against SGLT2.

[Chemical Formula 1]

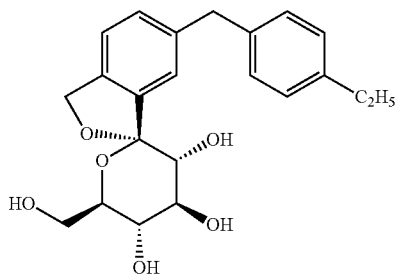

(I)

Further, WO 2009/154276 (Patent Document 2) discloses a monohydrate crystal, a co-crystal with sodium acetate, and a co-crystal with potassium acetate of the compound represented by formula (I). The document further discloses that the monohydrate crystal (hereafter referred to as crystal form I) has peaks at diffraction angles (2θ) of about 3.5°, 6.9°, 10.4°, 13.8°, 16.0°, 17.2°, 18.4°, 20.8°, 21.4°, and 24.4° in X-ray powder diffraction pattern; the co-crystal with sodium acetate has peaks at diffraction angles (2θ) of about 4.9°, 8.7°, 9.3°, 11.9°, 12.9°, 14.7°, 16.0°, 17.1°, 17.7°, 19.6°, 21.6° and 22.0° in X-ray powder diffraction pattern; and the co-crystal with potassium acetate has peaks at diffraction angles (2θ) of about 5.0°, 10.0°, 10.4°, 12.4°, 14.5°, 15.1°, 19.0°, 20.1°, 21.4° and 25.2° in X-ray powder diffraction pattern.

Furthermore, WO 2012/115249 (Patent Document 3) discloses a monohydrate crystal of the compound represented by formula (I), and the monohydrate crystal (hereafter referred to as crystal form II) is characterized as having peaks at diffraction angles (2θ) of about 4.0°, 7.5°, 10.8°, 12.7°, 14.0°, 14.7°, 18.0°, 18.8°, 19.5°, and 22.7° in X-ray powder diffraction pattern. The document further discloses that an acetone-water solvate crystal (hereafter referred to as crystal form III) of the compound represented by formula (I) has peaks at diffraction angles (2θ) of about 11.0°, 12.3°, 19.2°, 20.2°, and 21.6° in X-ray powder diffraction pattern.

A pharmaceutical preparation containing a low-melting point drug significantly deteriorates in quality due to melting of the drug during storage at a high temperature, and this has been problematic. In powders or granules, melting of a drug causes coagulation. In tablets, melting of a drug causes problems, such as oozing of the drug, mottling, or changing in color, during storage, and adhesion of the tablet material to the tableting machine at tableting (sticking). To cope with such problems, JP 2006-160730 A (Patent Document 4) discloses producing granules from a mixture of an adsorbing carrier, such as calcium silicate, magnesium hydroxide-aluminium hydroxide co-precipitate, or synthetic hydrotalcite, with a low-melting point drug, as a means for handling problems, such as oozing of a low-melting point substance and coagulation of powders and granules, that arise during storage at a high temperature as well as tableting defects such as sticking. Further, JP H10-287561 A reports a solid preparation obtained by adsorbing ibuprofen having a low melting point on a porous excipient, such as calcium silicate or light silicic anhydride.

JP S56-145214 A (Patent Document 6) discloses obtaining tablets by adding silicates to a low-melting point substance as a stabilizer to increase the eutectic point and prevent melting of the substance, thereby to reduce variation in the content of the low-melting point substance from tablet to tablet and reduce changes in properties such as dissolution and hardness. JP S63-243034 A (Patent Document 7) discloses a solid preparation obtained by blending a low-melting point substance with calcium silicate that adsorbs the substance, thereby to reduce sticking. JP 2000-239185 A (Patent Document 8) discloses a pharmaceutical composition which has been granulated using light silicic anhydride to reduce, for example, sticking and the influence on stimulatory components (e.g., bitterness). JP 2005-104934 A (Patent Document 9) discloses a composition obtained by melting a low-melting point substance by initially blending it with calcium silicate, so as to prevent tablet-to-tablet variation in drug content at tabletting caused by melt of the low-melting point substance or to prevent prolonged disintegration time (to improve stability during storage).

From the production point of view, tablets are largely divided into following groups: compressed tablets, which are produced by compressing a medicine to a certain shape, and molded tablets, which are produced by moistening the ingredients of a medicine with a solvent and forming, or molding, the moistened mixture into a certain shape. The production of the compressed tablets is the highest of all dosage forms. Examples of typical production methods of the compressed tablets include direct powder compression (direct compression) and wet granulation compression. The direct compression is a process by which a medicinal agent and additives in powder form are mixed and the mixture is directly compressed into tablets. This process requires the fewest steps and is economical, whereas it may cause problems such as insufficient tablet hardness, powdery tablet surface, and lack of content uniformity from tablet to tablet or within each tablet. The wet granulation is a process in which a medicinal agent and additives are granulated by wet method and the granules are pressed into tablets. Although this process requires many steps, it is widely used due to many advantages it offers; for example, a medicinal agent is easy to be distributed uniformly in tablets, and covering the surface of a poorly water-soluble medicinal agent with a hydrophilic polymer (binder) can improve the dissolution and hardness of the tablets as well as prevent powders from appearing on the tablet surfaces (Non-Patent Document 1).

CITATION LIST

Patent Documents

Patent Document 1: WO 2006/080421
Patent Document 2: WO 2009/154276
Patent Document 3: WO 2012/115249
Patent Document 4: JP 2006-160730 A
Patent Document 5: JP H10-287561 A
Patent Document 6: JP S56-145214 A
Patent Document 7: JP S63-243034 A
Patent Document 8: JP 2000-239185 A
Patent Document 9: JP 2005-104934 A

Non-Patent Documents

Non-Patent Document 1: Yamamoto, K, Editorial supervisor; "Basics of Science of Drug Formulation"; Elsevier Japan; Dec. 5, 2008; pp 126-129

SUMMARY OF INVENTION

Technical Problem

Nothing has been reported about solid preparations of tofogliflozin, which is a low-melting point compound (the crystal form I has a melting point of about 71° C.), that can be used as pharmaceuticals. In addition, the inventors of the present application have investigated the production of solid preparations of tofogliflozin and have found that conventional production methods and formulations would not give solid tofogliflozin preparations having sufficient disintegration and dissolution properties.

In view of the foregoing, an object of the present invention is to provide solid preparations containing tofogliflozin with improved disintegration and dissolution properties.

Solution to Problem

The inventors have found that mixing tofogliflozin with at least one filler, at least one disintegrant, and/or at least one lubricant, and then tableting the mixture by direct compression can produce tablets with improved disintegration and dissolution properties. Further, the inventors have found that the disintegration and dissolution properties can be improved by adjusting the weight ratio of calcium silicate to a certain low level.

The present invention has been attained based on such findings and, more specifically, the present invention provides the following [1] to [27].

[1] A pharmaceutical composition comprising tofogliflozin as an active ingredient, wherein the composition is a tablet obtained by direct compression of a powder mixture of at least one additive with tofogliflozin, and the additive comprises at least one excipient.

[2] The pharmaceutical composition of [1], wherein the excipient is selected from the group consisting of corn starch, potato starch, wheat starch, rice starch, partial alpha starch, alpha starch, lactose hydrate, fructose, glucose, mannitol, anhydrous dibasic calcium phosphate, crystalline cellulose, and precipitate calcium carbonate.

[3] The pharmaceutical composition of [1] or [2], wherein the additive further comprises at least one disintegrant.

[4] The pharmaceutical composition of [3], wherein the disintegrant is selected from the group consisting of sodium starch glycolate, carboxymethyl cellulose, carboxymethylcellulose calcium, carboxymethyl starch sodium, croscarmellose sodium, crospovidone, low substituted hydroxypropylcellulose, and hydroxypropyl starch.

[5] The pharmaceutical composition of any one of [1] to [4], wherein the additive further comprises at least one lubricant.

[6] The pharmaceutical composition of [5], wherein the lubricant is selected from the group consisting of magnesium stearate, calcium stearate, talc, sucrose fatty acid ester, sodium stearyl fumarate, and hydrogenated oil.

[7] The pharmaceutical composition of any one of [1] to [6], the composition being substantially free from calcium silicate.

[8] The pharmaceutical composition of any one of [1] to [7], wherein the tofogliflozin consists of a crystal form I, a crystal form II, a crystal form III, a co-crystal with sodium acetate, a co-crystal with potassium acetate, an amorphous form, or a mixture thereof.

[9] The pharmaceutical composition of [8], wherein the tofogliflozin consists of a crystal form I, a crystal form II, an amorphous form, or a mixture thereof.

[10] The pharmaceutical composition of any one of [1] to [9], wherein a weight ratio of the active ingredient tofogliflozin ranges from 2.5 to 40 wt % with respect to the total weight of the composition.

[11] The pharmaceutical composition of any one of [5] to [10], wherein the lubricant accounts for less than 4.0 wt % of the total weight of the composition.

[12] The pharmaceutical composition of any one of [3] to [11], wherein the excipient accounts for 20 to 80 wt % of the total weight of the composition and the disintegrant accounts for 1.0 to 4.0 wt % of the total weight of the composition.

[13] The pharmaceutical composition of any one of [1] to [12], wherein the additive contains excipients, a disintegrant, and a lubricant, the excipients being lactose hydrate and crystalline cellulose, the disintegrant being croscarmellose sodium, and the lubricant being hydrogenated oil, magnesium stearate, or a mixture thereof.

[14] A method for producing a pharmaceutical composition which is a tablet comprising tofogliflozin as an active ingredient, wherein the method comprises:
mixing an additive and tofogliflozin to prepare a powder mixture, and
obtaining a tablet from the powder mixture by direct compression,
wherein the additive comprises at least one excipient.

[15] The method of [14], wherein the excipient is selected from the group consisting of corn starch, potato starch, wheat starch, rice starch, partial alpha starch, alpha starch, lactose hydrate, fructose, glucose, mannitol, anhydrous dibasic calcium phosphate, crystalline cellulose, and precipitate calcium carbonate.

[16] The method of [14], wherein the additive further comprises at least one disintegrant.

[17] The method of [16], wherein the disintegrant is selected from the group consisting of sodium starch glycolate, carboxymethyl cellulose, carboxymethylcellulose calcium, carboxymethyl starch sodium, croscarmellose sodium, crospovidone, low substituted hydroxypropylcellulose, and hydroxypropyl starch.

[18] The method of any one of [14] to [17], wherein the additive further comprises at least one lubricant.

[19] The method of [18], wherein the lubricant is selected from the group consisting of magnesium stearate, calcium stearate, talc, sucrose fatty acid ester, sodium stearyl fumarate, and hydrogenated oil.

[20] The method of any one of [14] to [19], wherein wherein the composition is substantially free from calcium silicate.

[21] The method of any one of [14] to [20], wherein the tofogliflozin comprises a crystal form I, a crystal form II, a crystal form III, a co-crystal with sodium acetate, a co-crystal with potassium acetate, an amorphous form, or a mixture thereof.

[22] The method of [21], wherein the tofogliflozin comprises a crystal form I, a crystal form II, an amorphous form, or a mixture thereof.

[23] The method of any one of [14] to [22], wherein a weight ratio of the active ingredient tofogliflozin ranges from 2.5 to 40 wt % with respect to the total weight of the composition.

[24] The method of any one of [18] to [23], wherein the lubricant accounts for less than 4.0 wt % of the total weight of the composition.

[25] The method of any one of [16] to [24], wherein the filler accounts for 20 to 80 wt % of the total weight of the composition and the disintegrant accounts for 1.0 to 4.0 wt % of the total weight of the composition.

[26] The method of any one of [14] to [25], wherein the additive comprises lactose hydrate, crystalline cellulose, croscarmellose sodium, and hydrogenated oil and/or magnesium stearate.

[27] A solid preparation comprising tofogliflozin as an active ingredient, lactose hydrate, crystalline cellulose, croscarmellose sodium, and hydrogenated oil and/or magnesium stearate.

[28] The solid preparation of [27] having a dosage form selected from a tablet, a capsule, or a granule.

A skilled person in the art would appreciate that the present invention includes any one or any combination of two or more of the embodiments above, if they are technically consistent with one another based on common technical knowledge of those skilled in the art.

Advantageous Effects of Invention

According to the present invention, solid preparations with improved disintegration and dissolution properties are provided. Further, the invention provides a solid preparation with improved disintegration and dissolution properties by adjusting the weight ratio of calcium silicate, which is an additive of the solid preparation, to a low level. The use of the method of the present invention makes it possible to provide a solid preparation that allows a rapid release of a drug component.

Using the f2 function values obtained in Test Example 8, a factor analysis was performed using quality engineering (the Taguchi method, L18).

Figure 2:
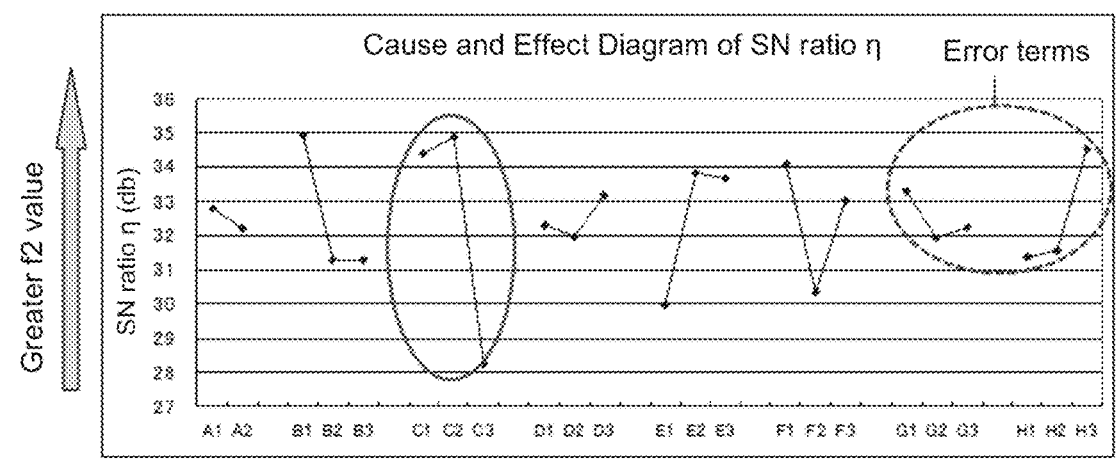

FIG. 2 is a cause and effect diagram that uses the condition levels (formulation condition) shown in Table 6.

Figure 3:
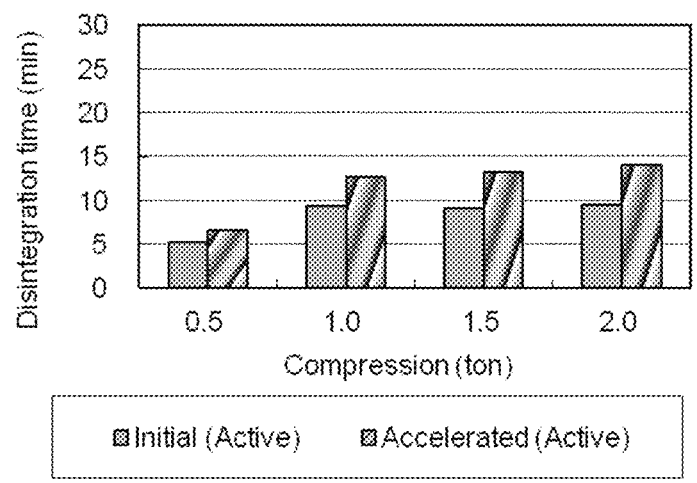

FIG. 3 is a diagram showing a relation between the disintegration time and the compression pressure for each of an initial product and an accelerated product of tablets containing 40 wt % of the active ingredient tofogliflozin hydrate (crystal form I) produced by direct compression (Test Example 1).

Figure 4:
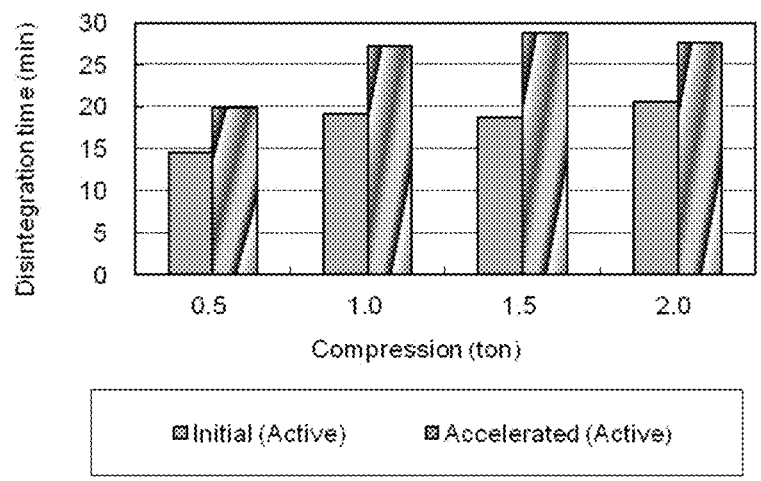

FIG. 4 is a diagram showing a relation between the disintegration time and the compression pressure for each of an initial product and an accelerated product of tablets containing 40 wt % of the active ingredient tofogliflozin hydrate (crystal form I) produced by wet granulation (Test Example 1).

DESCRIPTION OF EMBODIMENTS

The present invention relates to a pharmaceutical composition comprising tofogliflozin as an active ingredient, the composition being a tablet obtained by direct compression of a powder mixture of at least one additive with tofogliflozin, the additive comprising at least one filler. Further, the present invention relates to a method of producing the composition.

The term "tofogliflozin" as used in the present invention refers to a compound having the chemical name, 1,1-Anhydro-1-C-[5-(4-ethylphenyl)methyl-2-(hydroxymethyl)phenyl]-β-D-glucopyranose, and being represented by formula (I).

[Chemical Formula 2]

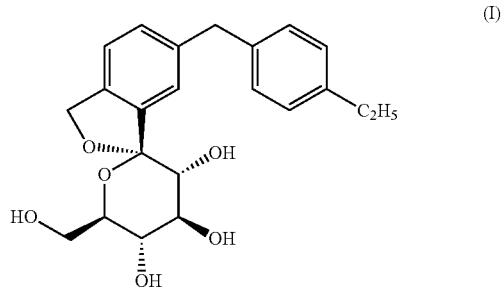

(I)

The "filler" as used in the present invention is exemplified by saccharides (e.g., lactose, lactose hydrate, fructose, glucose), sugar alcohols (e.g., mannitol), starches (e.g., corn starch, potato starch, wheat starch, rice starch, partial alpha starch, alpha starch), celluloses (e.g., crystalline cellulose) and inorganic salts (e.g., calcium silicate, anhydrous dibasic calcium phosphate, precipitate calcium carbonate), more specifically, corn starch, potato starch, wheat starch, rice starch, partial alpha starch, alpha starch, lactose hydrate, fructose, glucose, mannitol, anhydrous dibasic calcium phosphate, crystalline cellulose, and precipitate calcium carbonate, and more preferably, lactose and crystalline cellulose.

The "disintegrant" as used in the present invention is exemplified by starch, sodium glycolate, carboxymethyl cellulose, carboxymethylcellulose calcium, carboxymethyl starch sodium, croscarmellose sodium, crospovidone, low substituted hydroxypropylcellulose, and hydroxypropyl starch. More preferably, such a disintegrant is croscarmellose sodium, for example.

The "lubricant" as used in the present invention is exemplified by magnesium stearate, calcium stearate, talc, sucrose fatty acid ester, sodium stearyl fumarate, and hydrogenated oil. More preferably, such a lubricant is magnesium stearate or hydrogenated oil, for example.

In addition to the ingredients stated above, the solid preparation according to the present invention may contain typically used agents such as binders, lubricating and coloring agents, or flavoring agents, and also may contain, at need, stabilizers, emulsifiers, absorbefacients, surfactants, pH modifiers, antiseptics, antioxidants, or the like. The solid preparations may be formulated by combining ingredients commonly used as raw materials of solid preparations.

The "additive" as used in the present invention is intended to refer to ingredients commonly used as raw materials of solid preparations, examples of which may include fillers, disintegrants, lubricants, binders, lubricating and coloring agents, flavoring agents, stabilizers, emulsifiers, absorbefacients, surfactants, pH modifiers, antiseptics, and antioxidants.

The "solid preparation" as used herein refers to dosage forms such as tablets, powders, fine granules, granules, coated tablets, capsules, dry syrups, troches, suppositories. The dosage form refers to the form itself of a finished pharmaceutical product or the like. The dosage form of the solid preparation according to the present invention is preferably capsules, tables, or granules, and more preferably, capsules or tablets, but other forms may be used if they have ingredients typically used in the field of pharmaceutical formulation and typical shapes and sizes.

The hardness of tablets can be adjusted according to, for example, the type of additives used in preparing the tablets or the compression pressures. The compression pressure used in forming the pharmaceutical composition of the present invention ranges, for example, from 5 to 20 kN, more specifically, from 6.5 to 18.5 kN, and still more specifically, from 8 to 12 kN. Further, the hardness of the tablet of the pharmaceutical composition of the present invention ranges, for example, from 20 to 200 N, more specifically, from 30 to 150 N, and still more specifically, from 50 to 100 N.

Colorants that are allowed to be added to pharmaceuticals may be used in the composition. The flavoring agents to be used may include cocoa powder, menthol, aromatic powder, mentha oil, Borneo camphor, and cinnamon powder.

Of course, such tablets or granules may be coated with sugar coating or other suitable coating, as appropriate. Further, in producing a liquid preparation such as a syrup or injection, agents such as pH modifier, solvent, and tonicity agent, plus agents such as solubilizer and stabilizer, as appropriate, are added to a compound according to the present invention or a pharmacologically acceptable salt thereof to formulate the preparation.

The "crystal form I" as used in the present invention refers to a monohydrate crystal of the compound represented by formula (I). The monohydrate crystal is disclosed to have peaks at diffraction angles (2θ) of about 3.5°, 6.9°, 10.4°, 13.8°, 16.0°, 17.2°, 18.4°, 20.8°, 21.4°, and 24.4° in X-ray powder diffraction pattern (Patent Document 2).

The "crystal form II" as used in the present invention refers to a monohydrate crystal of the compound represented by formula (I). It is disclosed that the monohydrate crystal is characterized as having peaks at diffraction angles (2θ) of about 4.0°, 7.5°, 10.8°, 12.7°, 14.0°, 14.7°, 18.0°, 18.8°, 19.5°, and 22.7° in X-ray powder diffraction pattern (Patent Document 3).

The "crystal form III" as used in the present invention refers to an acetone-water solvate crystal of the compound represented by formula (I). It is disclosed that the acetone-water solvate crystal has peaks at diffraction angles (2θ) of about 11.0°, 12.3°, 19.2°, 20.2°, and 21.6° in X-ray powder diffraction pattern (Patent Document 3).

The "co-crystal with sodium acetate" as used in the present invention refers to a co-crystal with sodium acetate of the compound represented by formula (I). It is disclosed that the co-crystal with sodium acetate has peaks at diffraction angles (2θ) of about 4.9°, 8.7°, 9.3°, 11.9°, 12.9°, 14.7°, 16.0°, 17.1°, 17.7°, 19.6°, 21.6° and 22.0° in X-ray powder diffraction pattern (Patent Document 2).

The "co-crystal with potassium acetate" as used in the present invention refers to a co-crystal with potassium acetate of the compound represented by formula (I). It is disclosed that the co-crystal with potassium acetate has peaks at diffraction angles (2θ) of about 5.0°, 10.0°, 10.4°, 12.4°, 14.5°, 15.1°, 19.0°, 20.1°, 21.4° and 25.2° in X-ray powder diffraction pattern (Patent Document 2).

Preferably, tofogliflozin used in the solid preparation of the present invention is selected from the group consisting of a crystal form I, a crystal form II, a crystal form III, a co-crystal with sodium acetate, a co-crystal with potassium acetate, an amorphous form, or a mixture thereof. More preferably, tofogliflozin used in the solid preparation is selected from the group consisting of a crystal form I, a crystal form II, an amorphous form, or a mixture thereof. Still more preferably, tofogliflozin used in the solid preparation is a crystal form I. The proportions of crystal forms contained in tofogliflozin can be determined by using the NRI measurement, solid-state NMR, X-ray powder diffraction method, Raman spectrometry, or the like.

The solid preparation of the present invention is produced by mixing not only tofogliflozin and at least one filler but also at least one disintegrant and/or at least one lubricant and then direct compressing the mixture. Further, the present invention provides a method for producing a solid preparation that contains tofogliflozin, at least one filler, and at least one disintegrant and/or at least one lubricant and which is formed by direct compression.

The "direct compression" as used in the present invention refers to a process by which an active ingredient and additives in powder form are mixed and the mixture is directly compressed into tablets. The "wet granulation" refers to a process in which a medicinal agent and additives are granulated by wet method and the granules are pressed into tablets. The "wet method" refers to a process of producing granular mass by mixing a medicinal agent and an additive, and then spraying water directly on the powder mixture or placing a paste-form aqueous solution, in which a binder has been dissolved or dispersed, on the powder mixture.

The compression pressure used in tablet making may be adjusted depending on the ingredients or the required hardness of a tablet. The tablet hardness can be adjusted according to, for example, the type of additives used in preparing the tablet or the compression pressure. The compression pressure used in forming the pharmaceutical composition of the present invention ranges, for example, from 5 to 20 kN, more specifically, from 6.5 to 18.5 kN, and still more specifically, from 8 to 12 kN. Further, the tablet hardness of the pharmaceutical composition of the present invention ranges, for example, from 20 to 200 N, more specifically, from 30 to 150 N, and still more specifically, from 50 to 100 N.

The dose of the solid preparation according to the present invention may be selected based on the level of symptom, age, sex, body weight, route of administration, type of salt, specific type of disease, and the like.

The "substantially free from calcium silicate" as used in the present invention refers to that the solid preparation is produced by direct compression such that the weight ratio of calcium silicate in the preparation is preferably less than 2.5% or less than 2.0%, more preferably less than 1.75%, less than 1.5%, less than 1.25%, less than 1.0%, or less than 0.75%.

In a non-limiting embodiment of the present invention, it is preferable, but not limited to, that the solid preparation is substantially free from not only calcium silicate, but also light silicic anhydride, hydrated silicon dioxide, calcium silicate, magnesium hydroxide-aluminium hydroxide co-precipitate, synthetic aluminum silicate, synthetic hydrotalcite, or magnesium aluminometasilicate.

The "weight ratio" as used in the present invention refers to a ratio that compares the weight of an active ingredient or an additive with the total weight of the pharmaceutical preparation.

In an embodiment of the present invention, the weight ratio of tofogliflozin in the solid preparation is preferably, but not limited to, in the range of 1.0 wt % to 80 wt %, 1.0 wt % to 70 wt %, 1.0 wt % to 60 wt %, 1.0 wt % to 50 wt %, 2.5 wt % to 40 wt %, 10 wt % to 40 wt %, or 20 wt % to 40 wt %. The preparation can be produced by using tofogliflozin hydrate, and in that case, the weight ratio of tofogliflozin is calculated based on the weight of tofogliflozin contained in the hydrate.

From the viewpoint of preventing tableting defects, the weight ratio of tofogliflozin in the solid preparation is preferably, but not limited to, 60 wt % or less, 50 wt % or less, 40 wt % or less, 30 wt % or less, or 20 wt % or less. Further, the ratio is preferably, but not limited to, 1.0 wt % or more, 2.5 wt % or more, or 5.0 wt % or more.

In an embodiment of the present invention, the weight ratio of an filler in the solid preparation is preferably, but not limited to, in the rage of 5.0 wt % to 95 wt %, 10 wt % to 90 wt %, 15 wt % to 85 wt %, or 20 wt % to 80 wt %.

In an embodiment of the present invention, the total weight ratio of lactose hydrate and crystalline cellulose in the solid preparation is preferably, but not limited to, in the range of 5.0 wt % to 95 wt %, 10 wt % to 90 wt %, 15 wt % to 85 wt %, or 20 wt % to 80 wt %.

In an embodiment of the present invention, the weight ratio of a disintegrant in the solid preparation is preferably, but not limited to, 50 wt % or less, 30 wt % or less, 20 wt % or less, 10 wt % or less, 8.0 wt % or less, 6.0 wt % or less, 4.0 wt % or less, 2.0 wt % or less, or 1.0 wt % or less.

In an embodiment of the present invention, the weight ratio of croscarmellose in the solid preparation is preferably, but not limited to, 10 wt % or less, 8.0 wt % or less, 6.0 wt % or less, 4.0 wt % or less, 2.0 wt % or less, or 1.0 wt % or less. Further, the ratio is preferably, but not limited to, at least 0.1 wt % or at least 0.5 wt %.

In an embodiment of the present invention, the weight ratio of a lubricant in the solid preparation is preferably, but not limited to, less than 20 wt %, less than 10 wt %, less than 8.0 wt %, less than 6.0 wt %, less than 5.0 wt %, less than 4.0 wt %, less than 3.0 wt %, or less than 2.0 wt %. Further, the ratio is preferably, but not limited to, at least 0.1 wt %, at least 0.5 wt %, or at least 1.0 wt %.

In an embodiment of the present invention, the total weight ratio of hydrogenated oil and magnesium stearate in the solid preparation is preferably, but not limited to, less than 10 wt %, less than 8.0 wt %, less than 6.0 wt %, less than 5.0 wt %, less than 4.5 wt %, less than 4.0 wt %, less than 3.5 wt %, less than 3.0 wt %, or less than 2.5 wt %. Further, the ratio is also preferably, but not limited to, at least 0.1 wt %, at least 0.5 wt %, at least 1.0 wt %, or at least 1.5 wt %.

A non-limiting embodiment of the present invention provides a tablet that contains the active ingredient tofogliflozin in a weight ratio of 20%, lactose hydrate in a weight ratio of 55%, crystalline cellulose in a weight ratio of 20%, croscarmellose sodium in a weight ratio of 2%, and hydrogenated oil and magnesium stearate in total in a weight ratio of 3%.

When the term "and/or" was used in the context of expressing a combination of additives in the specification, the term refers to any possible combination of "and" and "or." More specifically, for example, an expression "fillers, disintegrants, and/or lubricants" refers to the following variations of additives: (a) fillers, (b) disintegrants, (c) lubricants, (d) fillers and disintegrants, (e) fillers and lubricants, (f) disintegrants and lubricants, and (g) fillers, disintegrants, and lubricants.

A skilled person in the art would appreciate that the present invention includes any one or any combination of two or more of the embodiments above if they are technically consistent with one another based on common technical knowledge of those skilled in the art.

The prior art documents cited are incorporated herein by reference in their entirely.

EXAMPLES

Comparative Example 1 (Wet Granulation, Tofogliflozin Hydrate Concentration=40%)

In accordance with the formulation and amounts shown in Table 1, tofogliflozin hydrate (crystal form I), lactose hydrate, crystalline cellulose, low substituted hydroxypropylcellulose, and hydroxypropylcellulose were mixed sufficiently in a mortar, and then 3.5 g of purified water was added to the mixture to produce wet granules. The granules were passed through a sieve of 710 μm mesh and then dried in an oven at a temperature of 50° C. for 4 hours. Subsequently, the dried granules were mixed with magnesium stearate in a poly bag. The resultant mixture was compressed using a tabletting device at each of compression pressures of 500 kgf, 1000 kgf, 1500 kgf, and 2000 kgf to form flat tablets (diameter; 7.5 mm, tablet weight; 200 mg). Sticking was observed at the compression pressures 500 kgf and 1000 kgf. Slight sticking was observed at the compression pressures 1500 kgf and 2000 kgf.

[Table 1]

TABLE 1

| Formulation and Amount | | |
| --- | --- | --- |
| Raw material | Formulation (%) | Amount (g) |
| Tofogliflozin hydrate (crystal form I) | 40.0 | 8.0 |
| Lactose hydrate | 34.0 | 6.8 |
| Crystalline cellulose | 15.0 | 3.0 |
| Low substituted hydroxypropylcellulose | 7.5 | 1.5 |
| Hydroxypropylcellulose | 3.0 | 0.6 |
| Magnesium stearate | 0.5 | 0.1 |
| Total | 100.0 | 20.0 |

Example 1 (Direct Compression, Tofogliflozin Hydrate Concentration=40%)

In accordance with the formulation and amounts shown in Table 2, tofogliflozin hydrate (crystal form I), lactose hydrate, crystalline cellulose, and low substituted hydroxypropylcellulose were mixed sufficiently in a V-shaped mixer, and magnesium stearate was added and mixed again to give a powder blend. The powder blend was compressed using a tableting device at each of compression pressures of 500 kgf, 1000 kgf, 1500 kgf, and 2000 kgf to form flat tablets (diameter, 7.5 mm; tablet weight, 200 mg). Sticking was observed at each of the pressures.

[Table 2]

TABLE 2

Formulation and Amounts

| Raw material | Formulation (%) | Amount (g) |
|---|---|---|
| Tofogliflozin hydrate (crystal form I) | 40.0 | 8.0 |
| Lactose hydrate | 27.5 | 5.5 |
| Crystalline cellulose | 25.0 | 5.0 |
| Low substituted hydroxypropylcellulose | 6.5 | 1.3 |
| Magnesium stearate | 1.0 | 0.2 |
| Total | 100.0 | 20.0 |

Test Example 1 (Results of Disintegration Test and Tablet Hardness Measurement on Comparative Example 1 and Example 1)

A disintegration test and a tablet hardness measurement were performed on the tablets obtained in Comparative Example 1 and Example 1. Table 3 shows the results. In tablet hardness, almost no difference was observed between the two examples. However, the disintegration time in Comparative Example 1 was 14.5 to 20.6 minutes, while that in Example 1 was 5.2 to 9.6 minutes. The results confirmed that, in the production of the solid pharmaceuticals containing 40 wt % tofogliflozin hydrate (crystal form I), the tablet produced by direct compression had a shorter disintegration time than the tablet produced by wet granulation, though they had the same level of tablet hardness.

[Table 3-1]

TABLE 3-1

Disintegration Test Results (Uncoated Tablet)

| Compression Pressure (kgf) | Disintegration Time (min) | |
|---|---|---|
| | Comparative 1 | Example 1 |
| 500 | 14.5 ± 0.3 | 5.2 ± 0.2 |
| 1000 | 19.1 ± 0.8 | 9.3 ± 0.3 |
| 1500 | 18.7 ± 1.0 | 9.2 ± 0.4 |
| 2000 | 20.6 ± 0.9 | 9.6 ± 0.2 |

*1: n = 3, the numerical value after "±" is standard deviation.

[Table 3-2]

TABLE 3-2

Tablet Hardness Test Results (Uncoated Tablet)

| Compression Pressure (kgf) | Tablet Hardness (N) | |
|---|---|---|
| | Comparative 1 | Example 1 |
| 500 | 136.3 ± 2.5 | 122.0 ± 2.0 |
| 1000 | 146.7 ± 4.7 | 141.0 ± 3.0 |
| 1500 | 135.7 ± 4.9 | 149.3 ± 2.1 |
| 2000 | 146.0 ± 6.6 | 142.7 ± 3.1 |

*2: n = 3, the numerical value after "±" is standard deviation.

To evaluate the influence of accelerated conditions (harsh conditions) on the tablets obtained in Comparative Example 1 and Example 1, a disintegration test was performed with samples which were prepared by storing the tablets for 4 hours at 40° C.-75% RH and then additional 2 hours at 60° C. The results are shown in Tables 3-3, 3-4 and FIGS. 3 and 4. The results showed that the disintegration time of the accelerated products were likely to increase in both Comparative Example 1 and Example 1. The drug substance is a low-melting point compound, and thus it has been inferred that part of the drug substance in the tablets melted during storage even at a temperature not higher than the melting point of the substance, resulting in the delay of disintegration.

[Table 3-3]

TABLE 3-3

Disintegration Test Results (Initial)

| Compression Pressure (kgf) | Disintegration Time (min) | |
|---|---|---|
| | Comparative 1 | Example 1 |
| 500 | 14.5 ± 0.3 | 5.2 ± 0.2 |
| 1000 | 19.1 ± 0.8 | 9.3 ± 0.3 |
| 1500 | 18.7 ± 1.0 | 9.2 ± 0.4 |
| 2000 | 20.6 ± 0.9 | 9.6 ± 0.2 |

*1: n = 3, the numerical value after "±" is standard deviation.

[Table 3-4]

TABLE 3-4

Disintegration Test Results (Accelerated)

| Compression Pressure (kgf) | Disintegration Time (min) | |
|---|---|---|
| | Comparative 1 | Example 1 |
| 500 | 19.9 ± 1.6 | 6.6 ± 0.5 |
| 1000 | 27.2 ± 1.7 | 12.8 ± 0.4 |
| 1500 | 28.8 ± 1.6 | 13.2 ± 0.4 |
| 2000 | 27.6 ± 2.7 | 14.1 ± 0.5 |

*2: n = 3, the numerical value after "±" is standard deviation.

Comparative Example 2 (Wet Granulation, Tofogliflozin Hydrate Concentration=20%)

In accordance with the formulation and amounts shown in Table 4, tofogliflozin hydrate (crystal form I), lactose hydrate, crystalline cellulose, low substituted hydroxypropylcellulose and hydroxypropylcellulose were mixed sufficiently in a mortar, and then 5.0 g of purified water was added to the mixture to produce wet granules. The granules were passed through a sieve of 710 μm mesh and then dried in an oven at a temperature of 50° C. for 4 hours. Subsequently, the dried granules were mixed with magnesium stearate in a poly bag. The resultant mixture was compressed using a tabletting device at each of compression pressures of 300 kgf, 500 kgf, 1000 kgf, and 1500 kgf to form flat tablets (diameter, 7.5 mm; tablet weight, 200 mg). No sticking was observed at any of the pressures.

[Table 4]

TABLE 4

| Raw material | Formulation (%) | Amount (g) |
|---|---|---|
| Tofogliflozin hydrate (crystal form I) | 20.0 | 4.0 |
| Lactose hydrate | 54.0 | 10.8 |
| Crystalline cellulose | 15.0 | 3.0 |
| Low substituted hydroxypropylcellulose | 7.5 | 1.5 |
| Hydroxypropylcellulose | 3.0 | 0.6 |
| Magnesium stearate | 0.5 | 0.1 |
| Total | 100.0 | 20.0 |

Example 2 (Direct Compression, Tofogliflozin Hydrate Concentration=20%)

In accordance with the formulation and amounts shown in Table 5, tofogliflozin hydrate (crystal form I), lactose hydrate, crystalline cellulose, and low substituted hydroxypropylcellulose were mixed sufficiently in a V-shaped mixer, and magnesium stearate was added and mixed again to give a powder blend. The powder blend was compressed using a tabletting device at each of compression pressures of 500 kgf, 1000 kgf, and 1500 kgf to form flat tablets (diameter, 7.5 mm; tablet weight, 200 mg). No sticking was observed at any of the pressures.

[Table 5]

TABLE 5

| Raw material | Formulation (%) | Amount (g) |
|---|---|---|
| Tofogliflozin hydrate (crystal form I) | 20.0 | 4.0 |
| Lactose hydrate | 47.5 | 9.5 |
| Crystalline cellulose | 25.0 | 5.0 |
| Low substituted hydroxypropylcellulose | 6.5 | 1.3 |
| Magnesium stearate | 1.0 | 0.2 |
| Total | 100.0 | 20.0 |

Test Example 2 (Results of Disintegration Test and Tablet Hardness Measurement on Comparative Example 2 and Example 2)

Figure 1:
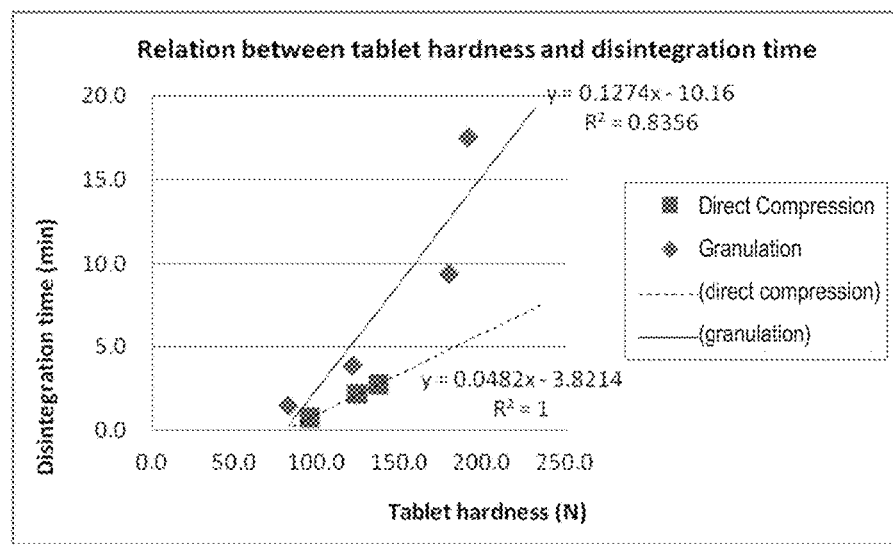
FIG. 1 is a diagram showing a relation between the hardness and the dissolution time of a tablet containing 20 wt % of the active ingredient tofogliflozin hydrate (crystal form I) for a case where the tablet was produced by direct compression and a case where the tablet was produced by wet granulation (Test Example 2).

A disintegration test and a tablet hardness measurement were performed on the tablets obtained in Comparative Example 2 and Example 2. Table 6 shows the results. The disintegration time ranged from 1.5 to 17.5 minutes in Comparative Example 2, whereas it ranged from 0.7 to 2.7 minutes in Example 2. The tablet hardness ranged from 81.7 to 190.7 N in Comparative Example 2, whereas it ranged from 94.4 to 136.3 N in Example 2. Since the two examples differed in tablet hardness, the relation of the hardness and the disintegration time was compared between the two production methods. This is shown in FIG. 1. The result confirmed that, at the same hardness, the disintegration time of the tablet produced by direct compression was significantly shorter than that of the tablet produced by wet granulation.

[Table 6-1]

TABLE 6-1

Disintegration Test Results (Uncoated Tablet)

| Compression Pressure (kgf) | Disintegration Time (min) | |
|---|---|---|
| | Comparative 2 | Example 2 |
| 300 | 1.5 ± 0.1 | not performed |
| 500 | 3.9 ± 0.3 | 0.7 ± 0.0 |
| 1000 | 9.4 ± 0.1 | 2.1 ± 0.0 |
| 1500 | 17.5 ± 1.0 | 2.7 ± 0.0 |

*1: n = 3, the numerical value after "±" is standard deviation.

[Table 6-2]

TABLE 6-2

Tablet Hardness Test Results (Uncoated Tablet)

| Compression Pressure (kgf) | Tablet Hardness (N) | |
|---|---|---|
| | Comparative 2 | Example 2 |
| 300 | 81.7 ± 5.9 | not performed coperformed |
| 500 | 120.7 ± 7.1 | 94.4 ± 3.1 |
| 1000 | 179.0 ± 1.7 | 123.7 ± 7.6 |
| 1500 | 190.7 ± 6.1 | 136.3 ± 1.5 |

*2: n = 3, the numerical value after "±" is standard deviation.

Examples 3 to 9 (Direct Compression: Investigation on Effects of Formulation, Drug Substance Concentration=20%)

The amounts of disintegrants and lubricants in formulations, which are commonly known to affect disintegration properties of pharmaceutical preparations, were varied to evaluate the effects on disintegration time. In the following Examples, the pharmaceuticals were prepared by adjusting the amount of tofogliflozin hydrate (crystal form I) such that the active ingredient tofogliflozin was contained in the amount shown in the table. In the process, an increase in the weight ratio of tofogliflozin hydrate due to hydrated water, was regulated by adjusting the weight ratio of lactose hydrate such that the total weight ratio was 100%.

In accordance with the formulation and amounts shown in Table 7, tofogliflozin hydrate (crystal form I), lactose hydrate, crystalline cellulose, and croscarmellose sodium were mixed sufficiently in a rotary drum mixer, and then hydrogenated oil and magnesium stearate were added and mixed again to give a powder blend. The powder blend was compressed using a rotary tablet press at each of compression pressures 6 kN, 8 kN, 10 kN, 12 kN, and 14 kN to form R tablets (diameter; 6.0 mm, tablet weight; 100 mg). Defects such as sticking and powdery tablet surface were not observed at any of the pressures.

[Table 7-1]

TABLE 7-1

| | Formulation | | | | | | |
|---|---|---|---|---|---|---|---|
| Ingredients | Example 3 | Example 4 | Example 5 | Example 6 | Example 7 | Example 8 | Example 9 |
| Tofogliflozin | 20.0 | 20.0 | 20.0 | 20.0 | 20.0 | 20.0 | 20.0 |
| Lactose hydrate (filler) | 55.0 | 56.0 | 53.0 | 56.0 | 54.0 | 56.5 | 52.5 |
| Crystalline cellulose (filler) | 20.0 | 20.0 | 20.0 | 20.0 | 20.0 | 20.0 | 20.0 |
| Croscarmellose sodium (disintegrant) | 2.0 | 1.0 | 4.0 | 2.0 | 2.0 | 2.0 | 2.0 |
| Hydrogenated oil (lubricant) | 1.5 | 1.5 | 1.5 | 1.5 | 1.5 | 0.0 | 4.0 |
| Magnesium stearate (lubricant) | 1.5 | 1.5 | 1.5 | 0.5 | 2.5 | 1.5 | 1.5 |
| Total (%) | 100.0 | 100.0 | 100.0 | 100.0 | 100.0 | 100.0 | 100.0 |

[Table 7-2]

TABLE 7-2

| | Amount | | | | | | |
|---|---|---|---|---|---|---|---|
| Ingredients | Example 3 | Example 4 | Example 5 | Example 6 | Example 7 | Example 8 | Example 9 |
| Tofogliflozin | 1.000 | 1.000 | 1.000 | 1.000 | 1.000 | 1.000 | 1.000 |
| Lactose hydrate (filler) | 2.750 | 2.800 | 2.650 | 2.800 | 2.700 | 2.825 | 2.625 |
| Crystalline cellulose (filler) | 1.000 | 1.000 | 1.000 | 1.000 | 1.000 | 1.000 | 1.000 |
| Croscarmellose sodium (disintegrant) | 0.100 | 0.050 | 0.200 | 0.100 | 0.100 | 0.100 | 0.100 |
| Hydrogenated oil (lubricant) | 0.075 | 0.075 | 0.075 | 0.075 | 0.075 | 0.000 | 0.200 |
| Magnesium stearate (lubricant) | 0.075 | 0.075 | 0.075 | 0.025 | 0.125 | 0.075 | 0.075 |
| Total (kg) | 5.000 | 5.000 | 5.000 | 5.000 | 5.000 | 5.000 | 5.000 |

Test Example 3 (Results of Disintegration Test and Tablet Hardness Measurement on Examples 3 to 9)

A disintegration test and a tablet hardness measurement were performed on the tablets obtained in Examples 3 to 9. Table 8 shows the results. In the hardness, no great difference was observed between the tablets, despite the difference in formulation. The disintegration time was within 5 minutes in any of the Examples, which confirmed that the tablets disintegrates rapidly. In particular, the tablets produced with the formulation in which the total weight ratio of the lubricants, namely, hydrogenated oil and magnesium stearate, was less than 4.0% (Examples 3, 4, 5, 6, and 8) were seen to disintegrate faster than the tablets with the formulation in which the total weight ratio of the lubricants was 4.0% or more (Examples 7 and 9), although the former was higher in tablet hardness than the latter.

[Table 8-1]

TABLE 8-1

| | Disintegration Test Results (Uncoated Tablet) | | | | | | |
|---|---|---|---|---|---|---|---|
| Compression Pressure | Example 3 | Example 4 | Example 5 | Example 6 | Example 7 | Example 8 | Example 9 |
| 6 kN | 1.5 ± 0.1 | 2.1 ± 0.1 | 2.2 ± 0.1 | 1.6 ± 0.0 | 2.4 ± 0.2 | 1.7 ± 0.1 | 3.0 ± 0.1 |
| 8 kN | 1.9 ± 0.1 | 2.5 ± 0.2 | 2.7 ± 0.1 | 2.0 ± 0.1 | 3.0 ± 0.1 | 2.1 ± 0.2 | 3.5 ± 0.1 |
| 10 kN | 2.4 ± 0.1 | 2.8 ± 0.1 | 2.8 ± 0.1 | 2.5 ± 0.1 | 3.0 ± 0.1 | 2.5 ± 0.1 | 3.7 ± 0.0 |
| 12 kN | 2.8 ± 0.1 | 3.2 ± 0.1 | 3.2 ± 0.0 | 2.8 ± 0.1 | 3.4 ± 0.1 | 2.7 ± 0.1 | 4.0 ± 0.1 |
| 14 kN | 3.1 ± 0.1 | 3.2 ± 0.1 | 3.2 ± 0.1 | 3.1 ± 0.0 | 3.5 ± 0.1 | 3.1 ± 0.1 | 4.0 ± 0.1 |

*1; n = 6, unit = min; target time = within 5 min; the numerical value after "±" is standard deviation.

[Table 8-2]

TABLE 8-2

| Tablet Hardness Results (Uncoated Tablet) | | | | | | | |
|---|---|---|---|---|---|---|---|
| Compression Pressure | Example 3 | Example 4 | Example 5 | Example 6 | Example 7 | Example 8 | Example 9 |
| 6 kN | 60.9 ± 3.5 | 63.8 ± 4.3 | 62.3 ± 2.4 | 63.6 ± 3.6 | 51.8 ± 3.5 | 62.1 ± 3.7 | 61.7 ± 3.0 |
| 8 kN | 69.6 ± 2.9 | 69.3 ± 2.8 | 70.5 ± 3.8 | 70.1 ± 4.0 | 58.5 ± 2.6 | 70.8 ± 2.8 | 67.3 ± 2.6 |
| 10 kN | 70.9 ± 4.6 | 73.9 ± 3.5 | 74.6 ± 5.2 | 72.3 ± 3.8 | 61.6 ± 3.5 | 77.8 ± 3.1 | 68.3 ± 3.0 |
| 12 kN | 75.3 ± 3.6 | not performed | 76.2 ± 4.2 | 76.3 ± 4.1 | 62.7 ± 2.6 | 78.7 ± 3.5 | 69.8 ± 3.2 |
| 14 kN | 78.6 ± 2.9 | 75.6 ± 3.4 | 78.5 ± 3.4 | 76.0 ± 4.0 | 65.3 ± 2.7 | 80.4 ± 3.4 | 71.5 ± 3.8 |

*1: n = 20; unit = N, target = 50 N or more; the numerical value after "±" is standard deviation.

Test Example 4 (Dissolution Test Results of Examples 3 to 9)

A dissolution test was performed on the tablets obtained at a compression pressure of 10 kN in Examples 3 to 9. Table 9 shows the results. In all these Examples, it was confirmed that 85% or more tofogliflozin was dissolved within 15 minutes and that the medicinal component was released rapidly.

[Table 9]

TABLE 9

| | Dissolution Test Results | | | | | | |
|---|---|---|---|---|---|---|---|
| | Example 3 | Example 4 | Example 5 | Example 6 | Example 7 | Example 8 | Example 9 |
| Dissolution rate in 15 min (%) | 99.8 ± 2.7 | 104.4 ± 2.5 | 97.9 ± 1.3 | 99.3 ± 1.5 | 98.4 ± 0.9 | 97.1 ± 3.3 | 102.4 ± 2.1 |

*1: n = 6; target = at least 85% dissolution in 15 min; the numerical value after "±" is standard deviation.

Example 3A (Direct Compression: Investigation of Effects of Acceleration on Dissolution Property, Drug Substance Concentration=20%)

To evaluate effects of acceleration on dissolution rate in 15 minutes, tofogliflozin hydrate (crystal form I), lactose hydrate, crystalline cellulose, and croscarmellose sodium, in accordance with the formulation and the amounts shown in Tables 9-1 and 9-2 (the formulation was the same as that of Example 3), were mixed sufficiently in a rotary drum mixer, and then hydrogenated oil and magnesium stearate were added and mixed again to give a powder blend. The amount of tofogliflozin hydrate (crystal form I) for use was adjusted such that the active ingredient tofogliflozin was contained in the amount shown in the table. In the process, an increase in the weight ratio of tofogliflozin hydrate due to hydrated water, was regulated by adjusting the weight ratio of lactose hydrate such that the total weight ratio was 100%. The powder blend was compressed using a rotary tablet press at each of compression pressures 10 kN, 14 kN, and 18 kN to form R tablets (diameter, 6.0 mm; tablet weight, 100 mg). No sticking was observed at any of the pressures.

[Table 9-1]

TABLE 9-1

| Formulation (%) | |
|---|---|
| Ingredients | Example 3A |
| Tofogliflozin | 20.0 |
| Lactose hydrate (filler) | 55.0 |
| Crystalline cellulose (filler) | 20.0 |

TABLE 9-1-continued

| Formulation (%) | |
|---|---|
| Ingredients | Example 3A |
| Croscarmellose sodium (disintegrant) | 2.0 |
| Hydrogenated oil (lubricant) | 1.5 |
| Magnesium stearate (lubricant) | 1.5 |
| Total (%) | 100.0 |

[Table 9-2]

TABLE 9-2

| Amount | |
|---|---|
| Ingredients | Example 3A |
| Tofogliflozin | 3.000 |
| Lactose hydrate (filler) | 8.250 |
| Crystalline cellulose (filler) | 3.000 |
| Croscarmellose sodium (disintegrant) | 0.300 |
| Hydrogenated oil (lubricant) | 0.225 |
| Magnesium stearate (lubricant) | 0.225 |
| Total (kg) | 15.000 |

Test Example 4A (Dissolution Test Results of Example 3A)

The tablet obtained at a compression pressure of 10 kN, 14 kN, or 18 kN in Example 3A was stored at 40° C.-75% RH, or at 40° C. in a sealed container, for 1 or 3 months to conduct a dissolution test. The results are shown in Table 9-4. In all the samples, it was confirmed that 85% or more tofogliflozin was dissolved within 15 minutes and that the medicinal component was released rapidly.

[Table 9-3]

TABLE 9-3

Dissolution Test Results (Dissolution rate in 15 min)

| Compression Pressure | 10 kN | 14 kN | 18 kN |
|---|---|---|---|
| Initial | 100.5 ± 0.3 | 97.5 ± 0.5 | 99.4 ± 1.3 |
| 40° C. - 75% RH 1M | 98.5 ± 1.4 | 97.7 ± 2.1 | 96.8 ± 2.8 |
| 40° C. - 75% RH 3M | 97.7 ± 3.1 | 97.9 ± 2.1 | 97.5 ± 1.7 |
| 40° C. sealed 1M | 99.8 ± 1.6 | 99.1 ± 0.9 | 99.4 ± 1.8 |
| 40° C. sealed 3M | 99.3 ± 1.1 | 99.3 ± 1.7 | 99.3 ± 1.4 |

*1: unit = %; n = 3; target = at least 85% dissolution in 15 min; the numerical value after "±" is standard deviation.

Examples 10 to 12 (Direct Compression: Investigation of Effects of Drug Substance Crystalline Form, Drug Substance Concentration=20%)

The tofogliflozin hydrate used in the tablet production contains three crystalline forms: crystal form I, crystal form II, and amorphous forms. Tablets were produced by using three types of the drug substance, each of which contains one of the crystalline forms at a higher proportion, to evaluate the effects on the disintegration time and tablet hardness. In producing the pharmaceuticals of the following Examples, the amount of tofogliflozin hydrate (crystal form I, crystal form II, and amorphous forms) was adjusted such that the active ingredient tofogliflozin was contained in the amount shown in the table. In the process, an increase in the weight ratio of tofogliflozin hydrate due to hydrated water, was regulated by adjusting the weight ratio of lactose hydrate such that the total weight ratio was 100%.

In accordance with the formulation and amounts shown in Table 10, tofogliflozin hydrate, lactose hydrate, crystalline cellulose, and croscarmellose sodium were mixed sufficiently in a rotary drum mixer, and then hydrogenated oil and magnesium stearate were added and mixed again to give a powder blend. The powder blend was compressed using a rotary tablet press at each of compression pressures 6 kN, 8 kN, 10 kN, 12 kN, and 14 kN to form R tablets (diameter, 6.0 mm; tablet weight, 100 mg). No sticking was observed at any of the pressures.

[Table 10-1]

TABLE 10-1

Proportions of Crystalline Forms in Drug Substance Used

|  | Example 10 (high in the content of crystal form I) | Example 11 (high in the content of crystal form II) | Example 12 (high in the content of amorphous form) |
|---|---|---|---|
| Crystal form I Proportion (%) | 93% | 18% | 47% |
| Crystal form II Proportion (%) | <0% | 53% | <0% |
| Amorphous form Proportion (%) | 8% | 29% | 58% |

[Table 10-2]

TABLE 10-2

Formulation and Amount: Used in Common in Examples 10-12

| Raw material | Formulation (%) | Amount (g) |
|---|---|---|
| Tofogliflozin | 20.0 | 900.0 |
| Lactose hydrate | 55.0 | 2475.0 |
| Crystalline cellulose | 20.0 | 900.0 |
| Croscarmellose Sodium | 2.0 | 90.0 |
| Hydrogenated oil | 1.5 | 67.5 |
| Magnesium stearate | 1.5 | 67.5 |
| Total | 100.0 | 4500.0 |

Test Example 5 (Dissolution Test Results and Tablet Hardness Measurements on Examples 10 to 12)

A disintegration test and a tablet hardness measurement were performed on the tablets obtained in Examples 10 to 12. Table 11 shows the results. In the hardness, no great difference was observed between the tablets, despite the difference in formulation. It was confirmed that the disintegration time was within 5 minutes in any of the Examples, and that the tablets disintegrated rapidly.

[Table 11-1]

TABLE 11-1

Disintegration Test Results (Uncoated Tablet)

| Compression Pressure | Example 10 | Example 11 | Example 12 |
|---|---|---|---|
| 6 kN | 1.3 ± 0.0 | 2.0 ± 0.1 | 1.5 ± 0.1 |
| 8 kN | 1.9 ± 0.1 | 2.7 ± 0.3 | 2.2 ± 0.1 |
| 10 kN | 2.1 ± 0.1 | 3.4 ± 0.2 | 2.6 ± 0.1 |
| 12 kN | 2.4 ± 0.1 | 4.1 ± 0.1 | 3.2 ± 0.1 |
| 14 kN | 2.7 ± 0.0 | 4.4 ± 0.2 | 3.5 ± 0.1 |

*1: n = 6, unit = min; target time = within 5 min; the numerical value after "±" is standard deviation.

[Table 11-2]

TABLE 11-2

Tablet Hardness Results (Uncoated Tablet)

| Compression Pressure | Example 10 | Example 11 | Example 12 |
|---|---|---|---|
| 6 kN | 55.6 ± 2.7 | 52.2 ± 3.1 | not performed |
| 8 kN | 58.2 ± 3.1 | 59.3 ± 3.0 | 53.1 ± 2.7 |
| 10 kN | 67.1 ± 4.1 | 66.5 ± 2.7 | 60.7 ± 2.6 |
| 12 kN | 64.0 ± 4.3 | 67.3 ± 3.3 | 57.5 ± 2.5 |
| 14 kN | 69.6 ± 2.9 | 70.6 ± 3.2 | 59.2 ± 2.9 |

*1: n = 20; unit = N; Target = at least 50N; the numerical value after "±" is standard deviation.

Comparative Example 3 (Test Formulation Prepared Using Information in the Patent Documents as Guide)

As described in Test Example 1, it turned out that a solid preparation containing tofogliflozin, the crystal form I of which has a melting point of about 71° C., has a problem in formulation specific to a low-melting point compound, namely, a delay in tablet disintegration. Thus, the inventors tried solving possible problems in formulation by mixing tofogliflozin hydrate (crystal form I) with calcium silicate, by reference to the Patent Documents described in BACKGROUND ART. In accordance with the formulation and amounts shown in Table 12, tofogliflozin hydrate (crystal form I), lactose hydrate, crystalline cellulose, croscarmellose sodium, and calcium silicate were mixed sufficiently in a V-shaped mixer, and magnesium stearate, talc, and hydrogenated oil were added and mixed again to give a powder blend. The amount of tofogliflozin hydrate (crystal form I) was adjusted such that the active ingredient tofogliflozin was contained in the amount shown in the table. In the process, an increase in the weight ratio of tofogliflozin hydrate due to hydrated water was regulated by adjusting the weight ratio of lactose hydrate such that the total weight ratio was 100%. The powder blend was compressed using a single tablet press at a pressure of 1000 kgf to form R tablets (diameter, 6 mm; tablet weight, 100 mg). No tableting defect was observed in the evaluation of handling (tablet weight variation), sticking, and creaking.

[Table 12]

TABLE 12

Formulation and Amount

| Raw material | Formulation (%) | Amount (g) |
|---|---|---|
| Tofogliflozin | 20.0 | 60.0 |
| Lactose hydrate | 42.0 | 126.0 |
| Crystalline cellulose (Prosolv) | 20.0 | 60.0 |
| Croscarmellose sodium | 6.0 | 18.0 |
| Calcium silicate | 5.0 | 15.0 |
| Magnesium stearate | 2.5 | 7.5 |
| Talc | 1.5 | 4.5 |
| Hydrogenated oil | 3.0 | 9.0 |
| Total | 100.0 | 300.0 |

Test Example 6 (Dissolution Test Results of Comparative Example 3)

With regard to the tablets obtained in Comparative Example 3, a dissolution test was performed on an initial product and an accelerated product which was obtained by storing an initial product at 50° C.-75% RH for 2 weeks. Further, the f2 functions of the initial and accelerated products were calculated from the dissolution rates in 5, 10, 15, and 20 minutes, where the greatest changes occurred in the rate (if the f2 function is 50 or higher, the samples before and after the acceleration were deemed comparable in the dissolution property). The results were shown in Table 13. The time for 85% dissolution of the initial product was 9.3 minutes, which confirmed a rapid dissolution of the drug component. On the other hand, the time for 85% dissolution of the accelerated product was 39.4 minutes, which confirmed that the acceleration caused a large dissolution delay in the tablet of this formulation.

[Table 13]

TABLE 13

Dissolution Test Results

| | Comparative Example 3 |
|---|---|
| Initial | 9.3 min |
| Accelerated | 39.4 min |
| F2 function | 10.1 |

Samples 1 to 18 (Formulation for Investigation of Cause of Dissolution Delay)

In accordance with the formulation and amounts shown in Tables 14 and 15, tofogliflozin hydrate (crystal form I), lactose hydrate, crystalline cellulose, croscarmellose sodium, and calcium silicate were mixed sufficiently in a V-shaped mixer, and magnesium stearate, talc, and hydrogenated oil were added and mixed again to give a powder blend. The amount of tofogliflozin hydrate (crystal form I) was adjusted such that the active ingredient tofogliflozin was contained in the amount shown in the table. In the process, an increase in the weight ratio of tofogliflozin hydrate due to hydrated water was regulated by adjusting the weight ratio of lactose hydrate such that the total weight ratio was 100%. The powder blend was compressed using a single tablet press at a pressure of 1000 kgf to form R tablets (diameter, 6 mm; tablet weight, 100 mg). No tableting defect was observed in the evaluation of handling (tablet weight variation), sticking, and cracking.

[Table 14-1]

TABLE 14-1

| | Formulation (%) | | | | | | | | |
|---|---|---|---|---|---|---|---|---|---|
| Raw material | Sample 1 | Sample 2 | Sample 3 | Sample 4 | Sample 5 | Sample 6 | Sample 7 | Sample 8 | Sample 9 |
| Tofogliflozin | 20.00 | 20.00 | 20.00 | 20.00 | 20.00 | 20.00 | 20.00 | 20.00 | 20.00 |
| Lactose hydrate | 57.50 | 53.00 | 48.50 | 53.25 | 48.75 | 51.00 | 49.50 | 49.50 | 48.00 |
| Crystalline Cellulose (Ceolus PH-101) | 20.00 | 20.00 | 20.00 | 20.00 | 20.00 | 20.00 | 20.00 | 20.00 | 20.00 |
| Croscarmellose Na | 2.00 | 2.00 | 2.00 | 4.00 | 4.00 | 4.00 | 6.00 | 6.00 | 6.00 |
| Ca Silicate | 0.00 | 1.25 | 2.50 | 0.00 | 1.25 | 2.50 | 0.00 | 1.25 | 2.50 |
| Mg Stearate | 0.50 | 1.50 | 2.50 | 0.50 | 1.50 | 2.50 | 1.50 | 2.50 | 0.50 |
| Talc | 0.00 | 0.75 | 1.50 | 0.75 | 1.50 | 0.00 | 0.00 | 0.75 | 1.50 |
| Hydrogenated oil | 0.00 | 1.50 | 3.00 | 1.50 | 3.00 | 0.00 | 3.00 | 0.00 | 1.50 |
| Total | 100.00 | 100.00 | 100.00 | 100.00 | 100.00 | 100.00 | 100.00 | 100.00 | 100.00 |

[Table 14-2]

TABLE 14-2

Formulation (%)

| Raw material | Sample 10 | Sample 11 | Sample 12 | Sample 13 | Sample 14 | Sample 15 | Sample 16 | Sample 17 | Sample 18 |
|---|---|---|---|---|---|---|---|---|---|
| Tofogliflozin | 20.00 | 20.00 | 20.00 | 20.00 | 20.00 | 20.00 | 20.00 | 20.00 | 20.00 |
| Lactose hydrate | 52.50 | 53.25 | 53.25 | 53.00 | 50.75 | 49.25 | 47.75 | 50.75 | 48.50 |
| Crystalline cellulose (Prosolv) | 20.00 | 20.00 | 20.00 | 20.00 | 20.00 | 20.00 | 20.00 | 20.00 | 20.00 |
| Croscarmellose Na | 2.00 | 2.00 | 2.00 | 4.00 | 4.00 | 4.00 | 6.00 | 6.00 | 6.00 |
| Ca Silicate | 0.00 | 1.25 | 2.50 | 0.00 | 1.25 | 2.50 | 0.00 | 1.25 | 2.50 |
| Mg Stearate | 2.50 | 0.50 | 1.50 | 1.50 | 2.50 | 0.50 | 2.50 | 0.50 | 1.50 |
| Talc | 1.50 | 0.00 | 0.75 | 1.50 | 0.00 | 0.75 | 0.75 | 1.50 | 0.00 |
| Hydrogenated oil | 1.50 | 3.00 | 0.00 | 0.00 | 1.50 | 3.00 | 3.00 | 0.00 | 1.50 |
| Total | 100.00 | 100.00 | 100.00 | 100.00 | 100.00 | 100.00 | 100.00 | 100.00 | 100.00 |

[Table 15-1]

TABLE 15-1

Amount (g)

| Raw material | Sample 1 | Sample 2 | Sample 3 | Sample 4 | Sample 5 | Sample 6 | Sample 7 | Sample 8 | Sample 9 |
|---|---|---|---|---|---|---|---|---|---|
| Tofogliflozin | 60.00 | 60.00 | 60.00 | 60.00 | 60.00 | 60.00 | 60.00 | 60.00 | 60.00 |
| Lactose hydrate | 172.50 | 159.00 | 145.50 | 159.75 | 146.25 | 153.00 | 148.50 | 148.50 | 144.00 |
| Crystalline Cellulose (Ceolus PH-101) | 60.00 | 60.00 | 60.00 | 60.00 | 60.00 | 60.00 | 60.00 | 60.00 | 60.00 |
| Croscarmellose Na | 6.00 | 6.00 | 6.00 | 12.00 | 12.00 | 12.00 | 18.00 | 18.00 | 18.00 |
| Ca Silicate | 0.00 | 3.75 | 7.50 | 0.00 | 3.75 | 7.50 | 0.00 | 3.75 | 7.50 |
| Mg Stearate | 1.50 | 4.50 | 7.50 | 1.50 | 4.50 | 7.50 | 4.50 | 7.50 | 1.50 |
| Talc | 0.00 | 2.25 | 4.50 | 2.25 | 4.50 | 0.00 | 0.00 | 2.25 | 4.50 |
| Hydrogenated oil | 0.00 | 4.50 | 9.00 | 4.50 | 9.00 | 0.00 | 9.00 | 0.00 | 4.50 |
| Total | 300.00 | 300.00 | 300.00 | 300.00 | 300.00 | 300.00 | 300.00 | 300.00 | 300.00 |

[Table 15-2]

TABLE 15-2

Amount (g)

| Raw material | Sample 10 | Sample 11 | Sample 12 | Sample 13 | Sample 14 | Sample 15 | Sample 16 | Sample 17 | Sample 18 |
|---|---|---|---|---|---|---|---|---|---|
| Tofogliflozin | 60.00 | 60.00 | 60.00 | 60.00 | 60.00 | 60.00 | 60.00 | 60.00 | 60.00 |
| Lactose hydrate | 157.50 | 159.75 | 159.75 | 159.00 | 152.25 | 147.75 | 143.25 | 152.25 | 145.50 |
| Crystalline cellulose (Prosolv) | 60.00 | 60.00 | 60.00 | 60.00 | 60.00 | 60.00 | 60.00 | 60.00 | 60.00 |
| Croscarmellose Na | 6.00 | 6.00 | 6.00 | 12.00 | 12.00 | 12.00 | 18.00 | 18.00 | 18.00 |
| Ca Silicate | 0.00 | 3.75 | 7.50 | 0.00 | 3.75 | 7.50 | 0.00 | 3.75 | 7.50 |
| Mg Stearate | 7.50 | 1.50 | 4.50 | 4.50 | 7.50 | 1.50 | 7.50 | 1.50 | 4.50 |
| Talc | 4.50 | 0.00 | 2.25 | 4.50 | 0.00 | 2.25 | 2.25 | 4.50 | 0.00 |
| Hydrogenated oil | 4.50 | 9.00 | 0.00 | 0.00 | 4.50 | 9.00 | 9.00 | 0.00 | 4.50 |
| Total | 300.00 | 300.00 | 300.00 | 300.00 | 300.00 | 300.00 | 300.00 | 300.00 | 300.00 |

Test Example 7 (Dissolution Test Results of Samples 1 to 18)

With regard to the tablets of Samples 1 to 18, a dissolution test was performed on an initial product and an accelerated product that was obtained by storing an initial product at 50° C.-75% RH for 2 weeks. Further, the f2 functions of the initial and accelerated products were calculated from the dissolution rates in 5, 10, 15, and 20 minutes, where greatest changes occurred in the rate. The results were shown in Table 16. The time for 85% dissolution of the initial products ranged from 7.4 to 12.1 minutes, which confirmed a rapid dissolution of the drug component. On the other hand, the time for 85% dissolution of the accelerated products ranged from 8.1 to 38.11 minutes. For samples 6, 9, 15, and 18, the dissolution time for 85% dissolution exceeded 15 minutes. This confirmed what formulations had a large dissolution delay under accelerated conditions.

[Table 16-1]

TABLE 16-1

| | Sample 1 | Sample 2 | Sample 3 | Sample 4 | Sample 5 | Sample 6 | Sample 7 | Sample 8 | Sample 9 |
|---|---|---|---|---|---|---|---|---|---|
| | \multicolumn{9}{c}{Time for 85% Drug Component to Dissolve (min)} |
| Initial | 9.7 | 7.4 | 8.9 | 7.6 | 9.4 | 8.4 | 10.2 | 8.9 | 8.4 |
| Accelerated | 9.0 | 8.8 | 9.6 | 9.8 | 8.6 | 19.6 | 8.1 | 9.8 | 22.4 |
| F2 function | 61.8 | 55.5 | 58.0 | 52.3 | 55.6 | 19.2 | 41.3 | 63.3 | 19.8 |

[Table 16-2]

TABLE 16-2

| | Sample 10 | Sample 11 | Sample 12 | Sample 13 | Sample 14 | Sample 15 | Sample 16 | Sample 17 | Sample 18 |
|---|---|---|---|---|---|---|---|---|---|
| | \multicolumn{9}{c}{Time for 85% Drug Component to Dissolve (min)} |
| Initial | 10.8 | 9.9 | 9.1 | 12.1 | 9.1 | 9.2 | 10.4 | 9.3 | 8.7 |
| Accelerated | 13.4 | 9.1 | 10.9 | 9.1 | 13.7 | 21.0 | 9.5 | 9.3 | 38.1 |
| F2 function | 52.6 | 47.5 | 59.5 | 49.4 | 40.7 | 21.6 | 59.3 | 76.2 | 10.5 |

*1: n = 3; target = at least 85% dissolution in 15 min.

Test Example 8

Using the f2 function values obtained in Test Example 7, a factor analysis was performed using quality engineering (the Taguchi method, orthogonal array L18: $2 \times 3^7$) to specify the cause of the dissolution delay. Condition levels (formulation condition) are shown in Table 17 and a cause and effect diagram is shown in FIG. 2. FIG. 2 shows that the SN ratio (f2 value) decreased as the level goes from C1 to C3. This indicated that the f2 value decreased as the amount of calcium silicate increased, which suggested that calcium silicate affects the dissolution delay after acceleration.

[Table 17-1]

TABLE 17-1

Analysis Factors and Condition Levels

| | | Level 1 (C1) | Level 2 (C2) | Level 3 (C3) |
|---|---|---|---|---|
| A | Crystalline cellulose | PH-101 | Prosolv | — |
| B | Croscarmellose Na | 2 | 4 | 6 |
| C | Calcium silicate | 0 | 1.25 | 2.5 |
| D | Mg Stearate | 0.5 | 1.5 | 2.5 |
| E | Talc | 0 | 0.75 | 1.5 |
| F | Hydrogenated oil | 0 | 1.5 | 3 |
| G | no setting | — | — | — |
| H | no setting | — | — | — |

[Table 17-2]

TABLE 17-2

Allocation Table of Comparative Examples 4 to 21

| Sample No. | A | B | C | D | E | F | G | H |
|---|---|---|---|---|---|---|---|---|
| 1 | 1 | 1 | 1 | 1 | 1 | 1 | 1 | 1 |
| 2 | 1 | 1 | 2 | 2 | 2 | 2 | 2 | 2 |
| 3 | 1 | 1 | 3 | 3 | 3 | 3 | 3 | 3 |
| 4 | 1 | 2 | 1 | 1 | 2 | 2 | 3 | 3 |
| 5 | 1 | 2 | 2 | 2 | 3 | 3 | 1 | 1 |
| 6 | 1 | 2 | 3 | 3 | 1 | 1 | 2 | 2 |
| 7 | 1 | 3 | 1 | 2 | 1 | 3 | 2 | 3 |
| 8 | 1 | 3 | 2 | 3 | 2 | 1 | 3 | 1 |
| 9 | 1 | 3 | 3 | 1 | 3 | 2 | 1 | 2 |
| 10 | 2 | 1 | 1 | 3 | 3 | 2 | 2 | 1 |
| 11 | 2 | 1 | 2 | 1 | 1 | 3 | 3 | 2 |
| 12 | 2 | 1 | 3 | 2 | 2 | 1 | 1 | 3 |
| 13 | 2 | 2 | 1 | 2 | 3 | 1 | 3 | 2 |
| 14 | 2 | 2 | 2 | 3 | 1 | 2 | 1 | 3 |
| 15 | 2 | 2 | 3 | 1 | 2 | 3 | 2 | 1 |
| 16 | 2 | 3 | 1 | 3 | 2 | 3 | 1 | 2 |
| 17 | 2 | 3 | 2 | 1 | 3 | 1 | 2 | 3 |
| 18 | 2 | 3 | 3 | 2 | 1 | 2 | 3 | 1 |

[Reference Example 1] Disintegration Test Method

The test was conducted on specified quantity of tablets using a disintegration tester (of Toyama Sangyo Co.) in accordance with the procedure described in Japanese Pharmacopoeia to determine the dissolution time for each tablet. The test liquid was water of a temperature of 37±2° C. From the obtained measurements, the mean value and standard deviation were calculated.

[Reference Example 2] Tablet Hardness Measurement Method

The test was performed on specified quantities of tablets using a tablet hardness tester (of Pharma Test Co.) to determine the hardness for each tablet. From the obtained measurements, the mean value and standard deviation were calculated.

[Dissolution Test Method]

The dissolution time was determined for quantities of tablets using a dissolution tester (of Hanson Co.) under the following conditions. The test liquid was water (900 mL, 37±2° C.). The paddle rotation was set to 50 rpm and the sampling times were set to 2, 5, 10, 15, 20, 30, and 60 minutes. The obtained samples were analyzed by using high performance liquid chromatography.

[F2 function Calculation Method]

In accordance with the following equation, an f2 function was calculated. The dissolution rates in 5, 10, 15, and 20 minutes, where greatest changes occurred in the rate, were used in the equation to evaluate a similarity of the curves of initial and accelerated tablets.

$$f_2 = 50 \times \log\left\{\left[1 + (1/n)\sum_{t=1}^{n}(R_t - T_t)^2\right]^{-0.5} \times 100\right\}$$ [Formula 1]

INDUSTRIAL APPLICABILITY

The use of the method of the present invention makes it possible to provide a solid preparation that allows a rapid release of a drug component.

The invention claimed is:

1. A method for producing a pharmaceutical composition which is a tablet comprising tofogliflozin as an active ingredient, wherein the tofogliflozin is present in a form of monohydrate crystal, wherein the method comprises:
   mixing an additive and tofogliflozin to prepare a powder mixture, and
   obtaining a tablet from the powder mixture by direct compression,
   wherein the additive comprises at least one filler, and at least one lubricant,
   wherein the composition is substantially free from calcium silicate,
   wherein a weight ratio of the active ingredient tofogliflozin ranges from 2.5 to 40 wt % with respect to the total weight of the composition, and
   wherein a weight ratio of the lubricant ranges from less than 4.0 wt % of the total weight of the composition.

2. The method of claim 1, wherein the filler is selected from the group consisting of corn starch, potato starch, wheat starch, rice starch, partial alpha starch, alpha starch, lactose hydrate, fructose, glucose, mannitol, anhydrous dibasic calcium phosphate, crystalline cellulose, and precipitate calcium carbonate.

3. The method of claim 1, wherein the additive further comprises at least one disintegrant.

4. The method of claim 3, wherein the disintegrant is selected from the group consisting of sodium starch glycolate, carboxymethyl cellulose, carboxymethylcellulose calcium, carboxymethyl starch sodium, croscarmellose sodium, crospovidone, low substituted hydroxypropylcellulose, and hydroxypropyl starch.

5. The method of claim 1, wherein the lubricant is selected from the group consisting of magnesium stearate, calcium stearate, talc, sucrose fatty acid ester, sodium stearyl fumarate, and hydrogenated oil.

6. The method of claim 3, wherein a weight ratio of the filler ranges from 20 to 80 wt % of the total weight of the composition and a weight ratio of the disintegrant ranges from 1.0 to 4.0 wt % of the total weight of the composition.

7. The method of claim 1, wherein the additive comprises lactose hydrate, crystalline cellulose, croscarmellose sodium, and hydrogenated oil and/or magnesium stearate.

8. A pharmaceutical composition which is a tablet produced by the method of claim 1.

* * * * *